United States Patent [19]

Paciorek et al.

[11] Patent Number: 4,707,556
[45] Date of Patent: Nov. 17, 1987

[54] BORON NITRIDE POLYMERIC PRECURSORS

[75] Inventors: Kazimiera J. L. Paciorek, Corona del Mar; Reinhold H. Kratzer, Irvine; David H. Harris, Sierra Madre; Wilfried Krone-Schmidt, Whittier, all of Calif.

[73] Assignee: Ultrasystems Defense and Space, Inc., Irvine, Calif.

[21] Appl. No.: 14,700

[22] Filed: Feb. 13, 1987

[51] Int. Cl.$^4$ .............................. C07F 7/02; C07F 7/10
[52] U.S. Cl. ...................................... 556/403; 501/96
[58] Field of Search ........................................ 556/403

[56] References Cited

U.S. PATENT DOCUMENTS

| | | | |
|---|---|---|---|
| 3,382,279 | 5/1968 | Horn et al. | 556/403 |
| 3,392,181 | 7/1968 | Horn et al. | 556/403 |
| 4,581,468 | 4/1986 | Paciorek et al. | 556/403 |

*Primary Examiner*—Paul F. Shaver
*Attorney, Agent, or Firm*—Grant L. Hubbard

[57] ABSTRACT

Silyl containing cyclic borazines are prepared by reacting chloroborazine with disilazanes.

4 Claims, No Drawings

BORON NITRIDE POLYMERIC PRECURSORS

RIGHTS OF THE GOVERNMENT

This invention was made with Government support under Contract N00014-85-C-0659 awarded by the Department of the Navy. The Government has certain rights in this invention.

FIELD OF THE INVENTION

The invention relates to synthesis of boron-nitrogen preceramic polymers, by reacting chloroborazine with disilazanes, and final transformation into carbon-free boron nitride.

BACKGROUND OF THE INVENTION

This invention relates to a novel composition of matter as represented by borazine rings joined by nitrogen bridges for applications as ceramics precursors. Ceramics such as BN, $B_4C$, SiC, and $Si_3N_4$ are of great importance commercially. However, due to their insolubility and nonfusibility, the processing of these materials into useful end products presents grave difficulties. A readily processible polymer which upon pyrolysis can be transformed into a ceramic offers a potential for ceramic fiber production, coatings, foams, and also as a binder for ceramic powders eliminating the use of additives (i.e. sintering aids). It is the principal object of this invention, therefore, to provide preceramic polymer soluble in organic solvents and a process for its preparation.

Another object of the invention is to provide a process for transforming the preceramic polymer into a boron nitride ceramic.

Other objects and advantages of the invention will become apparent to those skilled in the art upon consideration of the accompanying disclosure.

SUMMARY OF THE INVENTION

The present invention resides in the synthesis of the preceramic polymer of the general formula shown.

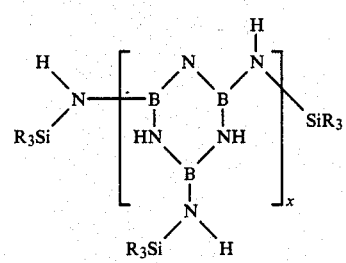

wherein R is an alkyl group such as methyl, ethyl, propyl, and butyl having the formula $C_nH_{2n+1}$ and x is a positive integer. The following reaction represents the synthesis process:

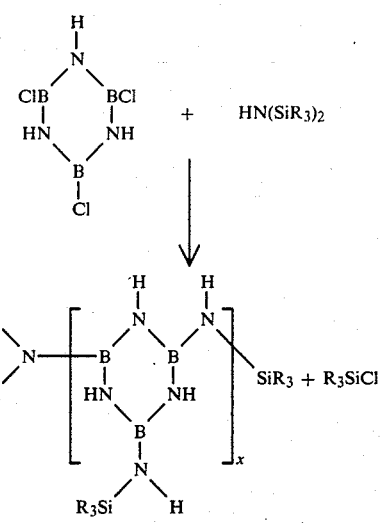

The procedure followed in the synthesis of the above material consists of an interaction of chloroborazine, a material described by C. A. Brown and A. W. Laubengayer, J. Am. Chem. Soc., 77, 3699–3700 (1955), with a disilazane. The reaction is usually conducted at temperatures ranging from $-78°$ C. to $0°$ C. from 4 to 24 hr, although longer or shorter periods can be used. The reaction is carried out under an inert gas such as nitrogen, helium, or argon. To obtain final boron nitride, either in a bulk form or as coatings on articles, the material is heated in an ammonia atmosphere gradually over a period of 4 to 24 hr from $25°$ to $1000°$ C.

A more complete understanding of the invention can be obtained by referring to the following illustrative examples, which are not intended, however, to be unduly limitative of the invention.

EXAMPLE I

Preparation of the Preceramic Polymers

Under nitrogen by-pass to a stirred solution of hexamethyldisilazane (11.3 g, 70.0 mmol) in hexane (120 ml) was added at $-50°$ to $-40°$ C. a solution of chloroborazine (2.5 g, 13.6 mmol) in 1:1 benzene/heptane (25 ml) over a period of 1.5 hr. Following the addition, the solution was stirred at $-35°$ C. for 1.5 hr; then the reaction mixture was allowed to warm up slowly to room temperature. The precipitate which formed, 0.6 g, was filtered off and on evaporation of the filtrate, 2.3 g of the preceramic polymer was obtained. Anal. calcd. for $C_{21}H_{89}N_{26}B_{17}Si_7$: C, 23.69; H, 8.42; N, 34.20; B, 15.23; Si, 18.46; MW, 1064.89. Found: C, 23.99; H, 8.20; N, 35.39; B, 14.88; MW, 1100. The material was very soluble in hexane, more than 480 mg/660 mg hexane.

EXAMPLE II

Bulk Boron Nitride Production

The preceramic polymer described in Example I, 102.5 mg, was heated in a platinum cup inserted into a quartz tube under 500 mm of ammonia from $25°$ to $990°$ C. over a period of 7 hr. The white residue weighed 37.6 mg which corresponds to 63.32% weight loss. Calcd. for $C_{21}H_{89}N_{26}B_{17}Si_7 \rightarrow 17BN$ weight loss is 65.04%. The material was completely colorless, free of carbon and did not melt or lose any weight when heated in air at $1000°$ C.

EXAMPLE III

Boron Nitride Fiber Production

From a 1:1 mixture of the preceramic polymer described in Example I and the preceramic polymer described by Kazimiera J. L. Paciorek, Reinhold H. Kratzer, D. H. Harris, Mark E. Smythe, and Patrick F. Kimble in U.S. Pat. No. 4,581,468 preceramic fibers were melt drawn. The preceramic polymer described in Example I imparts rigidity in the early stages of transformation to boron nitride which permits the process to proceed at a faster rate than possible in its absence. The fibers were transformed into boron nitride fibers by gradual heating in ammonia atmosphere from 68°-970° C. over a period of 25 hr. The fibers thus produced were completely colorless, free of carbon, and did not melt or lose any weight when heated in air or nitrogen at 1000° C.

As will be evident to those skilled in the art, modifications of the present invention can be made in view of the foregoing disclosure without departing from the spirit and scope of the invention.

We claim:

1. The polymer

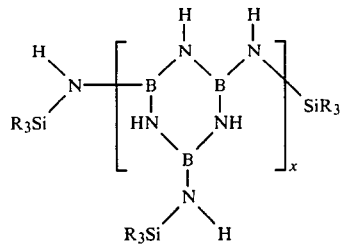

where R is methyl, ethyl propyl, or butyl of the general formula $C_nH_{2n+1}$ and where x is a positive integer.

2. The pentamer

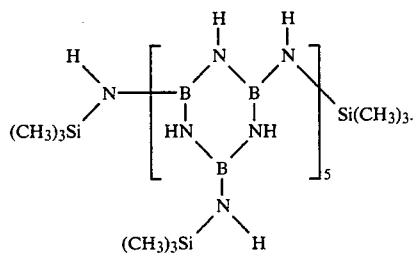

3. The process of preparing the polymer of claim 1 which comprises the steps of (1) reacting chloroborazine with a disilazane in a suitable solvent at temperatures $-78°$ to $0°$ C., (2) slow warm up to room temperature, (3) separation of the precipitated by-product by filtration, (4) isolation of the polymer by solvent removal.

4. A process in accordance with claim 3 wherein chloroborazine and hexamethyldisilazane are reacted in a benzene/hexane mixture as a solvent for a period from about 3 to 24 hr at $-50°$ to $-30°$ C.

* * * * *